United States Patent
Fraas et al.

(10) Patent No.: US 10,737,037 B2
(45) Date of Patent: Aug. 11, 2020

(54) SAFETY DEVICE FOR A SYRINGE

(71) Applicant: Gerresheimer Regensburg GmbH, Regensburg (DE)

(72) Inventors: Andreas Fraas, Amberg (DE); Maximilian Vogl, Mantel (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 177 days.

(21) Appl. No.: 15/573,065

(22) PCT Filed: Jun. 14, 2016

(86) PCT No.: PCT/EP2016/063651
§ 371 (c)(1),
(2) Date: Nov. 9, 2017

(87) PCT Pub. No.: WO2017/012783
PCT Pub. Date: Jan. 26, 2017

(65) Prior Publication Data
US 2018/0133409 A1    May 17, 2018

(30) Foreign Application Priority Data
Jul. 21, 2015    (DE) .................... 10 2015 111 835

(51) Int. Cl.
*A61M 5/32*  (2006.01)
*A61M 5/46*  (2006.01)

(52) U.S. Cl.
CPC .......... *A61M 5/3272* (2013.01); *A61M 5/326* (2013.01); *A61M 5/46* (2013.01); *A61M 2005/3267* (2013.01)

(58) Field of Classification Search
CPC .................... A61M 5/46; A61M 5/326; A61M 2005/3267; A61M 5/3271
See application file for complete search history.

(56) References Cited

U.S. PATENT DOCUMENTS 5,591,138 A * 1/1997 Vaillancourt ....... A61M 5/3271
                                                            604/192
5,688,241 A * 11/1997 Asbaghi ................ A61M 5/326
                                                            604/110
(Continued)

FOREIGN PATENT DOCUMENTS

DE    11 2009 001 083    3/2011
DE    10 2015 111 835    1/2017
(Continued)

OTHER PUBLICATIONS

U.S. Appl. No. 15/573,032, filed Nov. 9, 2017.
(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

The invention relates to a safety device, for avoiding stab wounds, for a syringe with a syringe body and with a puncturing means arranged at the distal end of the syringe body, said safety device comprising a sleeve element which extends along an axial direction (X) and at least partially encloses the puncturing means and the syringe body, wherein the sleeve element comprises, at its distal end, a contact portion which at least partially contacts the skin of a patient during use of the syringe and which delimits an opening surface. The safety device is characterized in that the opening surface has at least in part a sub-area that encloses an angle α with the axial direction (X), wherein the angle α is in a range of between 10° and 80°.

19 Claims, 6 Drawing Sheets

(56) References Cited

U.S. PATENT DOCUMENTS

| | | | |
|---|---|---|---|
| 5,944,700 A * | 8/1999 | Nguyen | A61M 5/46 604/117 |
| 2012/0265149 A1 | 10/2012 | Lerner et al. | |
| 2014/0378910 A1* | 12/2014 | Wong | A61M 5/3287 604/198 |
| 2015/0018773 A1* | 1/2015 | Evans | A61M 5/3272 604/198 |
| 2018/0104421 A1 | 4/2018 | Wittland et al. | |
| 2018/0110934 A1 | 4/2018 | Wittland et al. | |
| 2018/0161511 A1 | 6/2018 | Fraas et al. | |
| 2018/0161512 A1 | 6/2018 | Wittland et al. | |
| 2018/0161516 A1 | 6/2018 | Wittland et al. | |

FOREIGN PATENT DOCUMENTS

| | | |
|---|---|---|
| WO | WO 2004/032989 | 4/2004 |
| WO | WO 2009/137845 | 11/2009 |
| WO | WO 2013/134465 | 9/2013 |
| WO | WO 2017/012783 | 1/2017 |

OTHER PUBLICATIONS

U.S. Appl. No. 15/573,038, filed Nov. 9, 2017.
U.S. Appl. No. 15/573,047, filed Nov. 9, 2017.
U.S. Appl. No. 15/573,052, filed Nov. 9, 2017.
U.S. Appl. No. 15/573,048, filed Nov. 9, 2017.
International Preliminary Report on Patentability, with English Translation, dated Feb. 1, 2018, corresponding to International Application No. PCT/EP2016/063651 (filed Jun. 14, 2016), parent of the present application, 18pp.
Search Report and Written Opinion, with English translation, dated Sep. 19, 2016, corresponding to International Application No. PCT/EP2016/063651 (filed Jun. 14, 2016), parent of the present application, 22 pp.
European Office Action, dated Dec. 12, 2019, in European Patent Application No. 16728970.1, 5 pp.

* cited by examiner

SAFETY DEVICE FOR A SYRINGE

CROSS-REFERENCE TO RELATED APPLICATIONS

This application is a U.S. National Stage Application under 35 U.S.C. § 371 of International Application No. PCT/EP2016/063651, filed Jun. 14, 2016, which claims the benefit and priority of German Patent Application No. 102015111835.1, filed Jul. 21, 2015, both of which are hereby incorporated by reference in their entirety to the extent not inconsistent herewith.

The invention relates to a safety device for a syringe for avoiding stabwounds, said syringe having a syringe body and a piercing means arranged at the distal end of the syringe body, which safety device comprises a sleeve element, which extends along an axial direction (X) and surrounds the piercing means and the syringe body at least in part, the sleeve element, at the distal end thereof, having a contact portion which is in contact with at least a portion of a patient's skin when using the syringe and which defines an opening face.

Generic safety devices for avoiding stab wounds are known in the art. The use of safety devices of this type is expedient in particular in pre-filled syringes. The handling of such syringes is very simple, as the medium does not have to be transferred into the syringe prior to administration. Furthermore, the likelihood of using an incorrect drug is very low, even in emergencies. For vaccines and countless other drugs, such syringes are now the first-choice primary packaging material. These syringes are usually made of glass or plastics material (for example COC, COP) and must be provided with protective caps in order to prevent damage to and/or contamination of the cannula before the syringe is used. Moreover, it is important to secure the cannula after the syringe has been used in order to prevent stab wounds. In this case, careless replacement of the protective cap on the cannula can cause stab wounds. Often, the user cannot find the corresponding protective cap or forgets to replace said cap, leading to an avoidable risk of injury.

Accordingly, needle guards have been developed which are rigidly connected to the syringe and automatically receive the needle again after the syringe has been used. A needle guard of this kind is disclosed for example in DE 11 2009 001 083 T5. Said document discloses a spring-driven safety sleeve which, when extended, surrounds the cannula and prevents said cannula from causing injury to the user. The safety sleeve has a curved path in which at least one guide pin moves, thus allowing for different positions of the safety sleeve depending on the needle tip.

In this case, the at least one guide pin must be fastened to the front geometry of the syringe by means of a collar, or must be rigidly connected to the syringe in another manner. To preclude tampering or incorrect use, it must be impossible, or possible only with difficulty, to remove the collar together with the guide pin from the syringe comprising a cannula. Accordingly, a correspondingly secure fit in the axial direction is necessary.

Generic safety sleeves of this type are designed to be substantially rotationally symmetrical. As a result, said safety sleeves allow for only perpendicular injection of the contents of the syringe. In addition to this 90° injection, however, there are fields of application which require a 45° injection. A 45° injection of this type is required for example for patients who have a particularly thin layer of fat, or when active ingredients are to be injected into other layers of the body. By means of the existing safety devices, it is only possible to carry out such an injection, which is at a specific angle deviating from 90°, with difficulty or by circumventing the safety function. Thus, for example the safety sleeve is already incorrectly pulled back and held in position before the injection. An improper use of this type can lead to an increased risk of needle-prick injuries. Furthermore, in the prior art, there are safety devices, which have a needle that already protrudes to a great extent in the starting state in order to allow such injections deviating from 90°. Such a solution is disclosed for example in WO 2013/134465 A1. However, solutions of this type can be considered to be unsafe by nature, since the safety function of the safety device is impaired. In addition, the procedure with the safety sleeve is uncomfortable for the patient after the injection has taken place, since an edge of the safety sleeve presses on the skin at certain points.

The object of the present invention is therefore that of providing a safety device for a syringe for avoiding stab wounds, which solves the problems mentioned at the outset.

This object is achieved by a safety device for a syringe for avoiding stab wounds, said syringe having a syringe body and a piercing means arranged at the distal end of the syringe body, which safety device comprises a sleeve element, which extends along an axial direction (X) and surrounds the piercing means and the syringe body at least in part, the sleeve element, at the distal end thereof, having a contact portion which is in contact with at least a portion of a patient's skin when using the syringe and which defines an opening face. The safety device is characterised in that at least a portion of the opening face comprises a segment which forms an angle $\alpha$ together with the axial direction (X), the angle $\alpha$ being in a range between 10° and 80°.

By means of such a configuration of the safety device, it is possible to carry out an injection at an angle deviating from 90° and, at the same time, the safety function of the safety device is ensured before, during and after the injection. The opening face, through which the piercing means passes when using the syringe, is accordingly oriented at an angle $\alpha$ to the axial direction (X) or to a fictive plane which is at a right angle to the axial direction. During an injection, this fictive plane would correspond to the insertion surface on the skin. The angle $\alpha$ can be dimensioned according to requirements. Until now, an injection at a specific angle was carried out more or less by feel and was thus very dependent on the user. In this case, as a type of teaching, the safety device according to the invention would significantly improve the quality (adherence to the angle $\alpha$) of the puncture produced.

Advantageously, by combining the dimensioning of the angle $\alpha$ with the dimensioning of the length of the piercing means or of the maximum extension of the piercing means from the safety device, it is possible to define a puncture depth of the piercing means in a very precise manner. Accordingly, individual syringes can be provided which make it possible to carry out an injection in a specific body region at a specific puncture depth.

Advantageously, by combining the dimensioning of the angle $\alpha$ with the dimensioning of the length of the piercing means and/or of a maximum extent to which the piercing means emerges from the safety device, it is possible to define a puncture depth of the piercing means in a patient's skin. The maximum extent to which the piercing means emerges from the safety device can be understood to mean the maximum proportion of the length of the piercing means which can maximally protrude beyond the opening face. Accordingly, individual syringes can be provided which make it possible to carry out an injection in a specific body region at a specific puncture depth.

Preferably, the angle α is in a range between 20° and 70° and is more preferably 45°. In particular, injections at an angle of 45° are frequently used in medicine.

According to a particularly preferred concept of the invention, the safety device comprises a collar element which can be arranged on the distal end region of the syringe body and locks the safety device on the syringe body along the axial direction. To preclude tampering with or incorrect use of the syringe, it must be impossible or only possible with difficulty to remove the safety device from the syringe comprising a cannula. Accordingly, a correspondingly secure fit in the axial direction is necessary.

Preferably, the collar element comprises at least one guide projection which engages in at least one guide track of the sleeve element, the guide projection being guided in the at least one guide track of the sleeve element substantially along the axial direction (X) when the syringe body moves relative to the sleeve element. More preferably, the collar element is arranged on the distal end region of the syringe body so as to be rotatable in a circumferential direction (U). When the syringe is being used, the syringe, together with the safety device, is pressed against the patient's skin. The movement of the syringe body relative to the sleeve element and the guidance of the guide projection in the guide track cause the collar element to rotate in a circumferential direction (U). The sleeve element thus preferably slides over the syringe body, as a result of which the piercing means, which may be a cannula, a needle or a lancet, passes through a corresponding opening in the sleeve element. Rotation of the sleeve element on the patient's skin, about the puncture site, is thus prevented.

According to a particularly preferred embodiment, the collar element is substantially in the form of a hollow circular cylinder. Preferably, the circular cylinder comprises a lateral face on which the at least one guide projection is arranged. Preferably, the at least one guide projection extends radially away from the lateral face. More preferably, the guide projection is in the form of a circular cylinder or a pin. Advantageously, two diametrically opposed guide projections are arranged on the lateral face. As a result, the sleeve element would also comprise two diametrically opposed guide tracks, in each of which a guide projection is guided.

According to a preferred embodiment, the collar element comprises a distal region in which the wall of the collar element comprises at least two slots which extend in the axial direction (X). Slots of this type make it possible to adapt the collar element to different syringe body shapes and/or syringe body diameters. Furthermore, the slots make it easier to attach the collar element to the syringe body. When attaching the collar element to the syringe body, the collar element is usually pushed onto the syringe body. If the syringe body now has a projection or thicker portion, which may serve to lock the collar element in the axial direction, for example, this can make attachment difficult. However, the advantageous slots allow the collar element to be widened slightly, with the result that said element can be pushed onto the syringe body more easily.

The syringe body is preferably designed as a hollow circular cylinder and has, in the distal end region thereof, a conical end piece on which the piercing means is arranged. Preferably, the syringe body is made of glass or a polymeric plastics material, preferably a polyolefin, for example polypropylene or polyethylene, particularly preferably of a cyclic olefin polymer (COP) or of a cyclic olefin copolymer (COC). More preferably, a projection, on which an end face of the distal end of the collar element can engage, is formed on the conical end piece, making it possible to lock the collar element and thus the safety device in the axial direction. More preferably, the safety device is also substantially in the form of a hollow circular cylinder.

According to another preferred concept of the invention, the contact portion comprises an end face. When the syringe is being used, said end face rests on the patient's skin. Accordingly, it is advantageous to increase the friction between the end face and the skin in order to prevent the syringe from slipping off. Accordingly, it is advantageous for said end face to have a roughened surface structure and/or to consist of a rubberised material. The end face can, for example, be roughened or can have a coating made of a roughened material.

According to another embodiment, the opening face comprises another segment which forms an angle β together with the axial direction (X), the angle β being in a range between 80° and 100°. The angle β is preferably 90°.

According to another advantageous concept of the invention, the at least one guide track comprises a first and a second track region, which are separated from one another by a fictive separating line extending along the axial direction (X) of the syringe body, the guide projection, in a starting position, being arrangeable in the first track region.

Preferably, in the starting position, a distal end of the piercing means is arranged inside the sleeve element in the axial direction (X). The opening face of the sleeve element is thus arranged over the distal end of the piercing means in the axial direction (X). Preferably, the guide projection can be moved from the first track region into an end position in the second track region by crossing the separating line when a distal end of the piercing means is arranged in the opening face when the syringe body moves relative to the sleeve element. Accordingly, the guide projection can be moved from the first track region to the second track region. This movement takes place when the guide projection crosses a fictive separating line which separates the first and the second track regions from one another. If the guide projection is in the first track region, i.e. in a starting position, the syringe has not yet been actuated, i.e. the piercing means has not yet left the safety device. If the guide projection is in the second track region, the piercing means has already left the safety device, making injection possible. When passing from the first track region to the second track region, that is to say precisely when the guide projection crosses the separating line, the distal end of the piercing means is in the opening face.

According to another embodiment, in the starting position, a distal end of the piercing means is arranged in the opening face.

It would also be conceivable for a distal end of the piercing means to protrude, in the starting position, beyond the sleeve element or the opening face in the axial direction (X). Accordingly, a distal end of the piercing means is arranged above the opening face in the axial direction. Such embodiments would be conceivable in the event that a correspondingly deep puncture depth is to be achieved.

Preferably, the safety device comprises at least one spring element which is operatively connected to the syringe body and counteracts the movement of the syringe body relative to the safety device. Accordingly, the piercing means remains inside the sleeve element until the intended use. During use, the sleeve element must be moved counter to the spring force so that the piercing means can pass through the opening in the sleeve element and can be moved into an injection position, respectively. After the syringe has been used, the sleeve element, driven by the spring force of the spring element, automatically slides back over at least part of the piercing means. The guidance of the guide projection in the guide track causes the collar element to rotate counter to the circumferential direction (U). The user is thus protected from stab wounds caused by the used, contaminated piercing means. Preferably, the spring element comprises a spiral spring. Other types of springs, however, are also conceivable, such as leg springs or torsion springs. It would furthermore be conceivable to form the spring element as an elastomer.

The guide projection can preferably be moved, by means of a track of the second track region, from the second track region into an end region, in which movement of the sleeve element relative to the syringe body substantially along the axial direction (X) is at least limited. A configuration of this kind at least limits, preferably prevents, further displacement of the sleeve element relative to the syringe body. Accordingly, the piercing means is prevented from leaving the safety device again after the syringe has been used.

According to another preferred concept, the safety device comprises a cap element which is arranged at the distal end of the sleeve element. It would be conceivable for a cap element of this type to make it possible to lock the sleeve element with regards to the movement of the syringe body relative to the sleeve element. Accordingly, the piercing means, which may be a cannula, a needle or a lancet, is effectively prevented from undesirably emerging from the safety device. Damage to and contamination of the piercing means are thus prevented. The user of the syringe must firstly remove the cap element from the sleeve element before the syringe can be used. The risk of inadvertent actuation of the syringe is thus also reduced. It would be conceivable to apply a marking or an instruction to the cap element. The user would thus be forced to observe this marking or the instruction before using the syringe. A marking or instruction of this type could have a colour-based and/or haptic and/or other design. In particular for embodiments of the safety device in which the distal end of the piercing means protrudes beyond the safety device even in the starting position, a cap element is expedient for protecting the piercing means against damage and the user against injury. Furthermore, it is conceivable for the cap element to comprise a piercing means protective device. Such a piercing means protective device could be made for example of a resilient material, for example rubber. A resilient material of this type helps reducing the risk of the piercing means being damaged. It would also be conceivable for the cap element to comprise an attachment face which abuts the contact portion and would thus be complementary thereto. A terminal distal end of the cap element could then be designed to be at a right angle to the axial direction (X). It is conceivable for the cap element or the sleeve element to have latching elements, by means of which the cap element can be fixed to the sleeve element. Other types of fixing means would also be conceivable, such as providing elements on the cap element and/or the sleeve element which engage in or around one another.

Preferably, the piercing means comprises a cut and a tip. Advantageously, the piercing means is arranged in such a way that the tip thereof is arranged in a direction which is diametrically opposed to the maximum height of the sleeve element. Such an orientation of the piercing means with respect to the sleeve element ensures an optimal puncture position, which results in the patient being caused less pain during the puncture. Piercing means, for example cannulas, comprise a cut. Frequently, what is known as a facet cut is used. The distal end of such a cannula accordingly usually has at least one angle of inclination and a tip which is arranged eccentrically at the edge of the cannula. If an injection is carried out at a specific angle, unfavourable positioning of the tip of the cannula with respect to the sleeve element can cause the patient unnecessary pain.

Further advantages, aims and properties of the present invention will be explained with reference to the following description of the accompanying drawings. Like components can have the same reference signs in the various embodiments.

Figure 1:
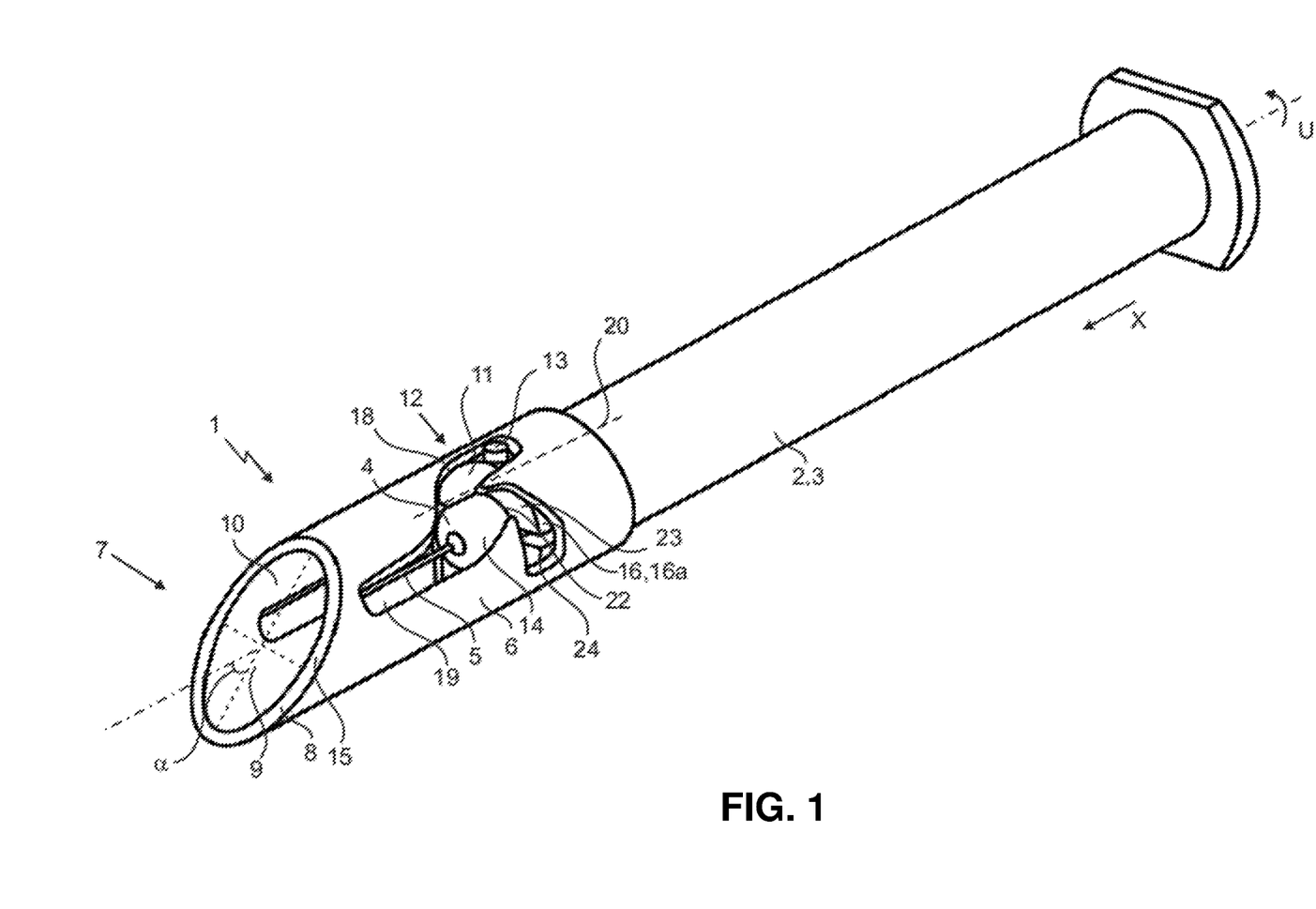
FIG. 1 is an isometric view of a syringe comprising a safety device.
Figure 2:
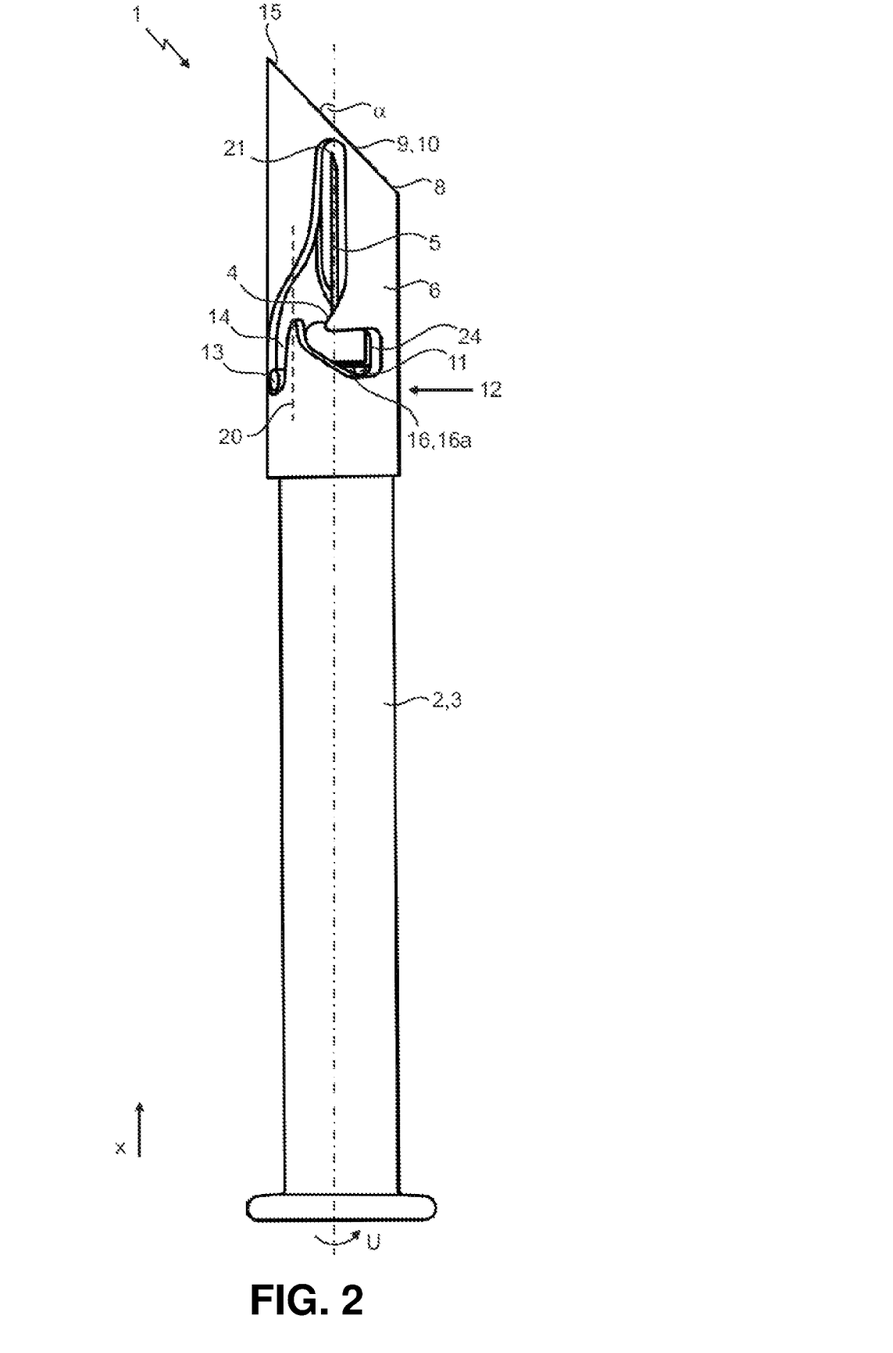
FIG. 2 is a side view of a syringe comprising a safety device.

In the drawings:

FIG. 2 is a side view of a syringe comprising a safety device according to a first embodiment.

The syringe (2) comprises a syringe body (3) configured as a hollow circular cylinder. The syringe body comprises a distal end region (12) having a distal end (4). Arranged at the distal end (4) is a piercing means (5). This piercing means (5) is connected via a hole in the distal end region (12) to the cavity in the syringe body (3), so that the medium to be injected during use of the syringe (2) can pass out of the cavity and through the piercing means (5). The distal end region (12) is designed as a conical end piece which has a smaller external diameter than the syringe body (3). The syringe also has a transition region in which the external diameter of the syringe body (3) transitions into the external diameter of the end piece.

The safety device (1) for a syringe (2) for avoiding stab wounds, said syringe having a syringe body (3) and a piercing means (5) arranged at the distal end (4) of the syringe body (3) comprises a sleeve element (6), which extends along an axial direction (X) and surrounds the piercing means (6) and the syringe body (3) at least in part. The sleeve element (6) comprises, at the distal end (7) thereof, a contact portion (8) which is contact with at least a portion of a patient's skin during use of the syringe (2), and which defines an opening face (9). At least a portion of the opening face (9) comprises a segment (10) which forms an angle α together with the axial direction (X), the angle α being in a range between 10° and 80°.

In this embodiment, the opening face comprises just one segment (10), and the angle α is 45°. The safety device (1) is substantially in the form of a hollow circular cylinder. Accordingly, the opening face (9) has an elliptical shape. By means of such a configuration of the safety device (1), it is possible to carry out an injection at an angle deviating from 90° and, at the same time, the safety function of the safety device (1) is ensured before, during and after the injection. The opening face, through which the piercing means passes when using the syringe, is accordingly oriented at an angle of 45° to the axial direction (X) or to a fictive plane which is at a right angle to the axial direction (X). During an injection, this fictive plane would correspond to the insertion surface on the skin. Until now, an injection at a specific angle was carried out more or less by feel and was thus very dependent on the user. In this case, as a type of teaching, the safety device (1) would significantly improve the quality (adherence to the 45° angle) of the puncture produced. The contact portion (8) that defines the opening face (9) comprises an end face (15). Said end face (15) is in contact with the patient's skin during use of the syringe (2). To prevent the syringe from slipping off, said end face (15) can have a roughened surface structure and/or be made of a rubberised material.

The safety device (1) further comprises a collar element (11) which can be arranged on the distal end region (12) of the syringe body (3). The safety device (1) is locked on the syringe body (3) with respect to the axial direction (X) by the collar element (11). Furthermore, the collar element (10) is substantially in the form of a hollow circular cylinder (16). The safety device is locked in the axial direction by a projection (22) or a thicker portion at the distal end (4) of the syringe body (3), against which projection or thicker portion the distal end (23) of the collar element (11) rests. Furthermore, the collar element (11) is arranged on the distal end region (12) of the syringe body (3) so as to be rotatable in a circumferential direction (U). The circular cylinder (16) further comprises a lateral face (16a), on which two guide projections (13) are arranged. The guide projections (13) extend radially outwards away from the lateral face (16a), and are arranged so as to be diametrically opposite one another. Furthermore, said projections are in the form of circular cylinders or pins. These two guide projections (13) each engage in one guide track (14) of the sleeve element (6) and are guided therein substantially in the axial direction (X) when the syringe body (3) moves relative to the sleeve element (6). In one embodiment, the safety device (1) further comprises a spring element (not shown in the drawings) which is operatively connected to the syringe body (3) and counteracts the movement of the sleeve element (6) relative to the safety device (1).

In the embodiment shown, the guide tracks (14) of the sleeve element (6) comprise a first (18) and a second (19) track region, which are separated from one another by a fictive separating line (20) extending along the axial direction (X) of the syringe body (3), the guide projection (13), in a starting position, being arrangeable in the first track region (18) and being moveable from the first track region (18) into an end position in the second track region (19) by crossing the separating line (20) when a distal end (21) of the piercing means (5) is arranged in the opening face (10) when the syringe body (3) moves relative to the sleeve element (6). In this embodiment, the distal end (21) of the piercing means (5), in the starting position, is arranged inside the sleeve element (6) in the axial direction (X). Accordingly, the opening face (9) is arranged over the distal end (21) of the piercing means (5) in the axial direction. The sleeve element (6) further comprises an end region (22). In this case, the guide projections (11) can be moved, by means of a track of the second track region (20), from the second track region (20) into an end region (24). In this end region (24), movement of the sleeve element (6) substantially along the axial direction (X) relative to the syringe body (3) is at least limited.

Figure 3:
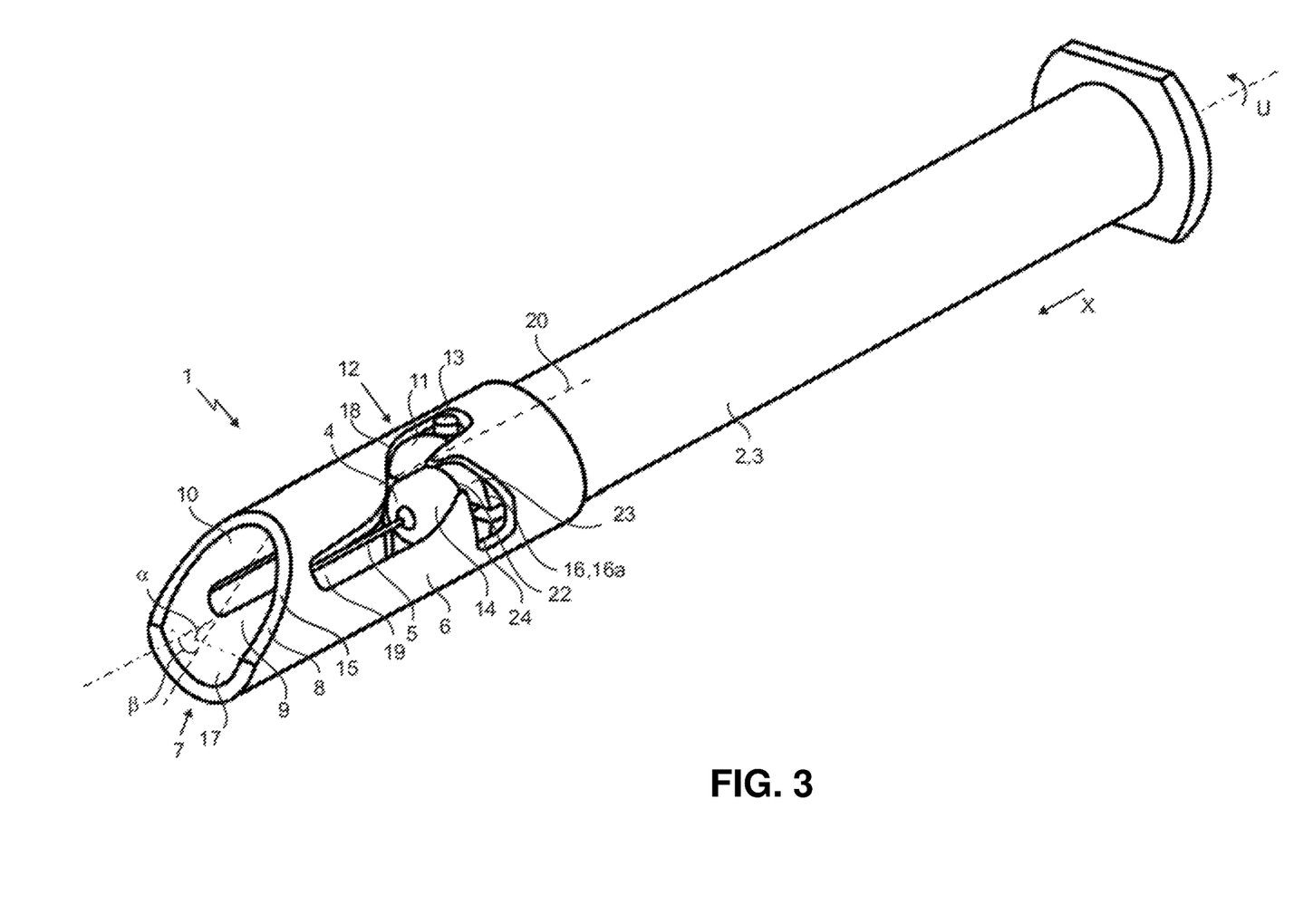
FIG. 3 is an isometric view of a syringe comprising a safety device according to another embodiment.
Figure 4:
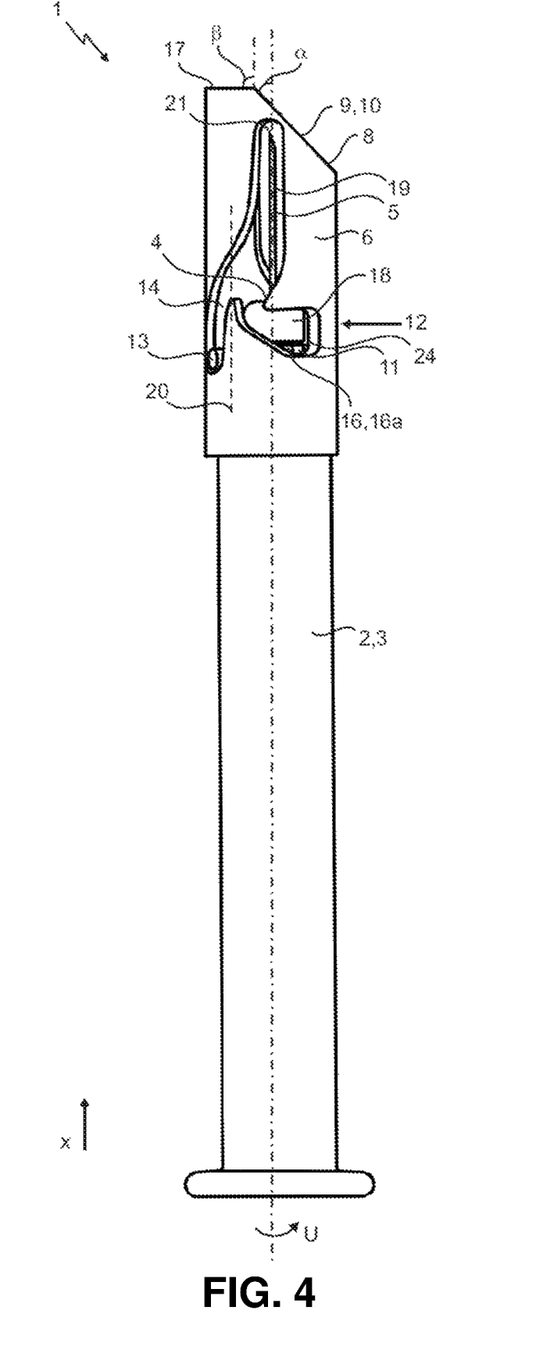
FIG. 4 is a side view of a syringe comprising a safety device according to another embodiment.

FIG. 3 is an isometric view of a syringe comprising a safety device, and FIG. 4 is a side view of a syringe comprising a safety device according to another embodiment. This embodiment differs from the previous embodiment only in terms of the design of the opening face (9). The opening face (9) comprises a first segment (10), which forms an angle α together with the axial direction (X), the angle α being in a range between 10° and 80°. The opening face (9) moreover comprises an additional segment (17), which forms an angle β together with the axial direction (X), the angle β being in a range between 80° and 100°. In this case, an angle α of 45° and an angle β of 90° would be selected. A segment (17) of this type, which extends perpendicularly to the axial direction (X), can be used as a bearing surface in the event of a perpendicular injection. However, it is also conceivable for said segment to be used to arrange a cap element on the sleeve element. For this purpose, said segment (17) can comprise fastening elements, for example latching elements. The first segment (10) is used, as in the previous embodiment, for an injection at an angle of 45°.

Figure 5:
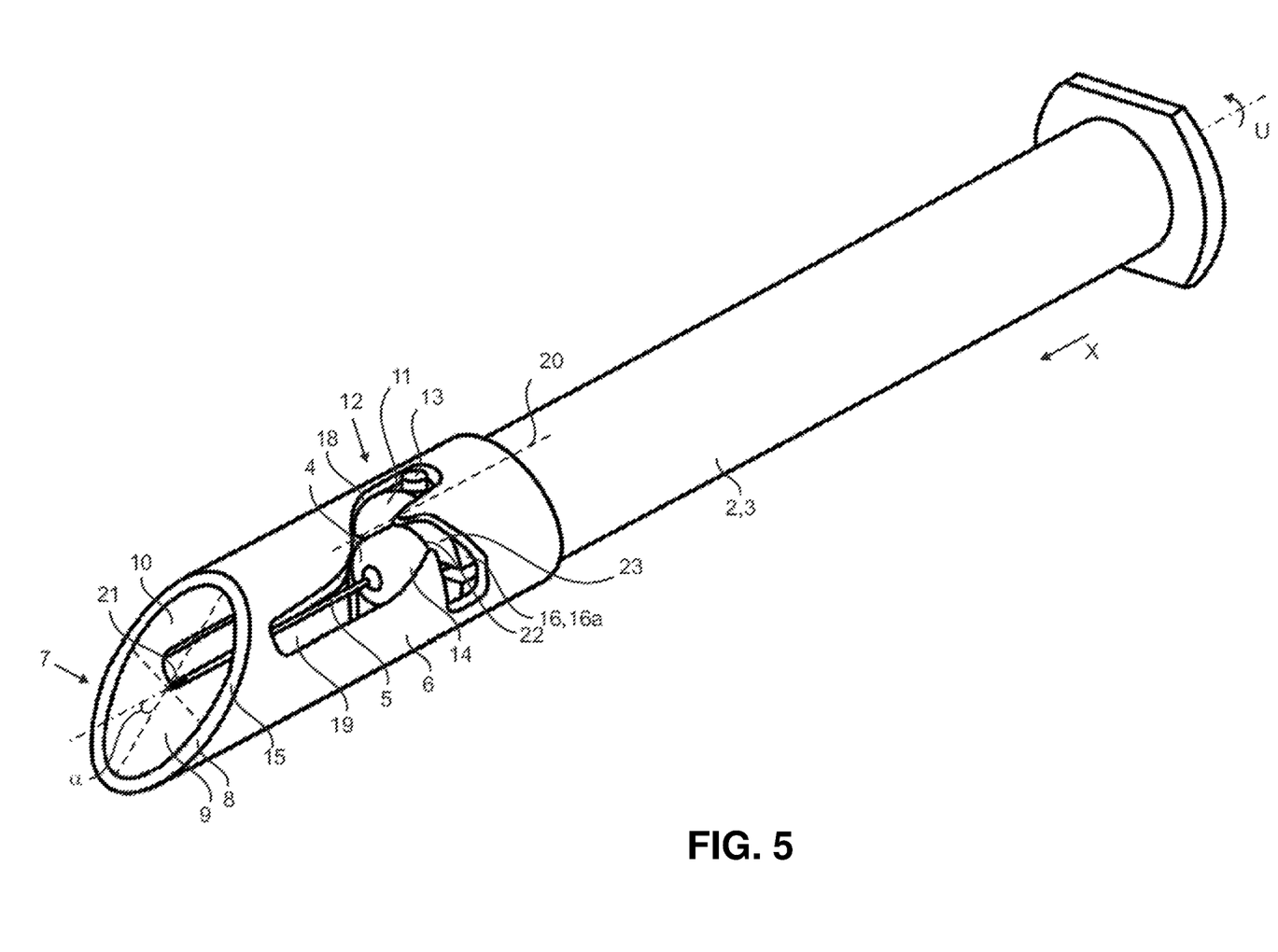
FIG. 5 is an isometric view of a syringe comprising a safety device according to another embodiment.
Figure 6:
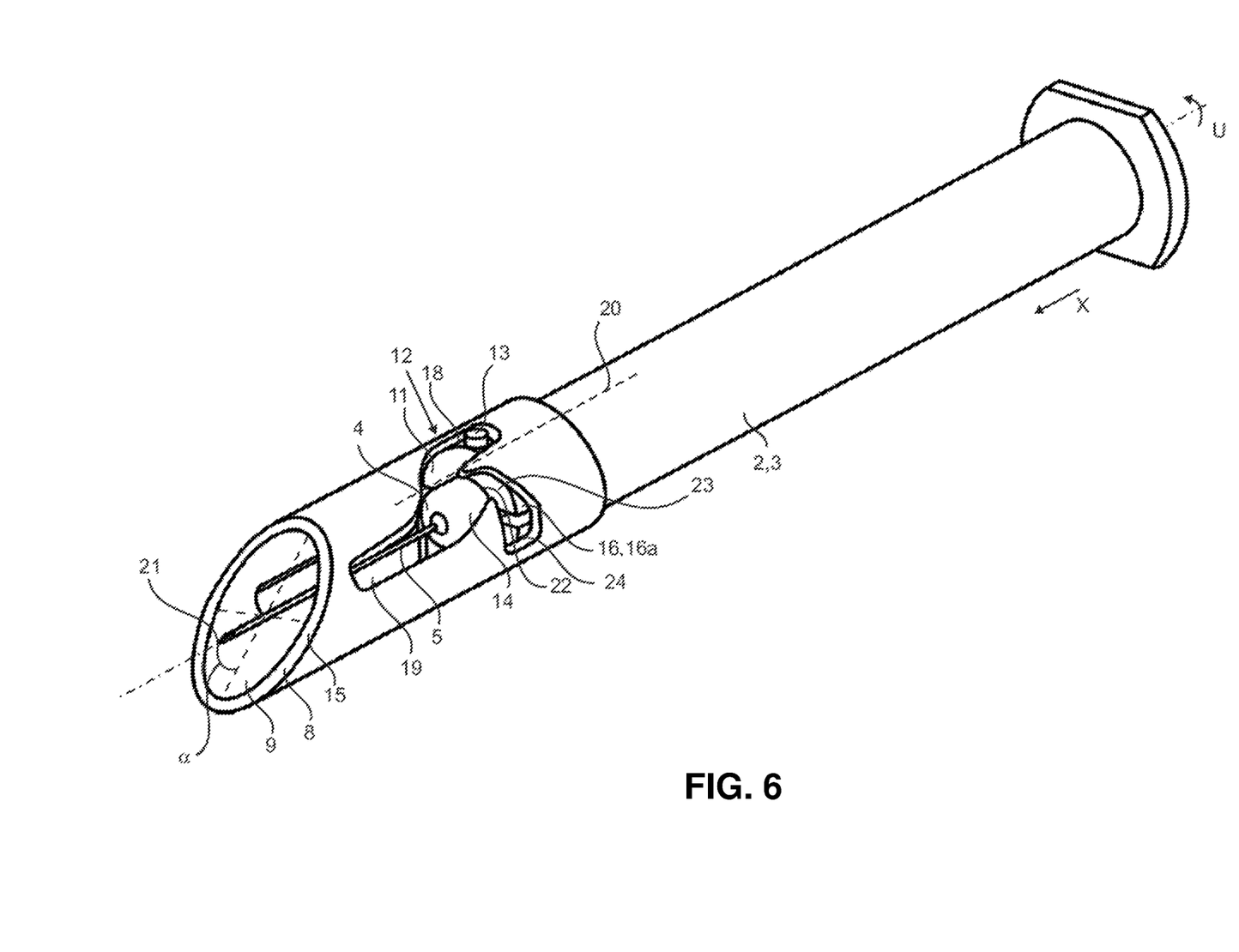
FIG. 6 is an isometric view of a syringe comprising a safety device according to another embodiment.

FIGS. 5 and 6 show embodiments of the safety device, which essentially correspond to the embodiment according to FIGS. 1 and 2. They differ merely in terms of the position of the distal end (21) of the piercing means (5) in the starting position. The guide tracks (14) comprise a first (18) and a second (19) track region, which are separated from one another by a fictive separating line (20) extending along the axial direction (X) of the syringe body (3), the guide projections (13), in the starting position, being arrangeable in the respective first track regions (18). In the embodiment shown in FIGS. 1 and 2, the distal end (21) of the piercing means (5), in the starting position, is arranged in the sleeve element, i.e. the opening face is arranged over the distal end (21) of the piercing means (5) in the axial direction (X). In FIG. 4, however, in the starting position, the distal end (21) of the piercing means (5) is arranged in the opening face (9). In FIG. 5, in the starting position, the distal end (21) of the piercing means (5) is arranged above the opening face (9) in the axial direction (X). The distal end (21) of the piercing means (5) thus protrudes beyond the sleeve element in the axial direction (X). By means of such embodiments, a correspondingly deep puncture depth can be achieved.

The piercing means (5) remains inside the sleeve element (6) until the intended use of the syringe (2). During use, the syringe is pressed against the patient's skin, the contact portion (8) of the sleeve element (6) or the end face (15) thereof being in contact with the patient's skin. Since at least a portion of the opening face (9) comprises a segment (10) which forms an angle α together with the axial direction (X), the injection can be carried out at a specific angle. The sleeve element (6) must be moved counter to the spring force of the spring element so that the piercing means (5) can be moved into the injection position. The sleeve element (6) is pushed over the distal end region (12) of the syringe body (3) in this case. The guidance of the guide projection (13) in the guide track (14) causes the collar element (11) to rotate along the circumferential direction (U). After the syringe (2) has been used, the sleeve element (6), driven by the spring force of the spring element, automatically slides back over at least a portion of the piercing means (5). The guidance of the guide projections (13) in the guide tracks (14) causes the collar element (11) to rotate counter to the circumferential direction (U).

All the features disclosed in the application documents are claimed as being essential to the invention, provided that they are novel over the prior art, either individually or in combination.

LIST OF REFERENCE SIGNS 1 safety device
2 syringe
3 syringe body 4 distal end of the syringe body
5 piercing means
6 sleeve element
7 distal end of the sleeve element
8 contact portion
9 opening face
10 segment of the opening face
11 collar element
12 distal end region of the syringe body
13 guide projection
14 guide track
15 end face of the contact portion
16 circular cylinder
16a lateral face of the circular cylinder
17 additional portion of the opening face
18 first track region
19 second track region
20 separating line
21 distal end of the piercing means
22 projection of the syringe body
23 distal end of the collar element
24 end region
X axial direction
U circumferential direction

The invention claimed is:

1. A syringe body comprising a piercing means arranged at the distal end of the syringe body and a safety device for avoiding stab wounds,
wherein the safety device comprises a sleeve element which extends along an axial direction (X) and surrounds the piercing means and the syringe body at least in part, the sleeve element, at the distal end thereof, having a contact portion which is in contact with at least a portion of a patient's skin when using the syringe and which defines an opening face, wherein:
at least a portion of the opening face comprises a segment which forms an angle α together with the axial direction (X), the angle α being in a range between 10° and 80°, the safety device comprising a collar element which is rotatably arranged on the distal end region of the syringe body and locks the safety device on the syringe body along the axial direction (X),
wherein the collar element comprises at least one guide projection which engages in at least one guide track of the sleeve element, the guide projection being guided in the at least one guide track of the sleeve element substantially in the axial direction (X) when the syringe body moves relative to the sleeve element, and
wherein the movement of the syringe body relative to the sleeve element and the guidance of the guide projection in the guide track cause the collar element to rotate in a circumferential direction (U) of the syringe body,
wherein the angle α is selected, and the length of the piercing means and/or a maximum extent to which the piercing means emerges from the safety device are selected, to provide a predetermined puncture depth of the piercing means in the patient.

2. The syringe body according to claim 1, wherein:
the angle α is in a range between 20° and 70°.

3. The syringe body according to claim 1, wherein:
the collar element being substantially in the form of a hollow circular cylinder, the circular cylinder having a lateral face on which the at least one guide projection is arranged.

4. The syringe body according to claim 1, wherein:
the contact portion comprises an end face which has a roughened surface structure and/or consists of a rubberized material.

5. The syringe body according to claim 1, wherein:
the opening face comprises another segment which forms an angle β together with the axial direction (X), the angle α being in a range between 80° and 100°.

6. The syringe body according to claim 1, wherein:
the guide track comprises a first and a second track region which are separated from one another by a fictive separating line extending along the axial direction (X) of the syringe body, the guide projection, in a starting position, being arrangeable in the first track region.

7. The syringe body according to claim 6, wherein:
in the starting position, a distal end of the piercing means is arranged inside the sleeve element in the axial direction (X), it being possible for the guide projection to be moved from the first track region into an end position in the second track region by crossing the separating line when a distal end of the piercing means is arranged in the opening face when the syringe body moves relative to the sleeve element.

8. The syringe body according to claim 6 wherein:
in the starting position, a distal end of the piercing means is arranged in the opening face.

9. The syringe body according to claim 6, wherein:
in the starting position, a distal end of the piercing means protrudes beyond the sleeve element in the axial direction (X).

10. The syringe body according to claim 1, wherein:
the safety device comprises at least one spring element which is operatively connected to the syringe body and counteracts the movement of the syringe body relative to the sleeve element.

11. The syringe body according to claim 1, wherein:
the at least one guide projection can be moved, by means of a track in the second track region, from the second track region into an end region in which movement of the sleeve element (6) relative to the syringe body substantially along the axial direction (X) is at least restricted.

12. The syringe body according to claim 1, wherein:
the safety device comprises a cap element which is arranged at the distal end of the sleeve element.

13. The syringe body according to claim 1, wherein:
the piercing means comprises a cut and a tip, the piercing means being arranged in such a way that the tip thereof is arranged in a direction which is diametrically opposed to the maximum height along an axial direction of the sleeve element.

14. The syringe body according to claim 1, wherein the collar element comprises a distal region in which a wall of the collar element comprises at least two slots which extend in the axial direction (X), wherein the slots make it possible to adapt the collar element to different syringe body shapes and/or syringe body diameters.

15. The syringe body according to claim 7, wherein the guide projection can be moved, by means of a track of the second track region, from the second track region into an end region, in which movement of the sleeve element relative to the syringe body substantially along the axial direction (X) is at least limited, wherein a further distal displacement of the sleeve element relative to the syringe body is prevented by an abutment of the guide projection to the end region of the guide track, and the guide projection in the end region of the guide track is substantially at the same height along an axial direction (X) as the guide projection in the starting position.

16. The syringe body according to claim 1, wherein an outer diameter of the sleeve element is constant along the entire extension of the sleeve element.

17. The syringe body according to claim 1, wherein the sleeve element encloses the collar element.

18. The syringe body according to claim 1, wherein the angle α is 45°.

19. A syringe body comprising a piercing means arranged at the distal end of the syringe body and a safety device for avoiding stab wounds,
   wherein the safety device comprises a sleeve element which extends along an axial direction (X) and surrounds the piercing means and the syringe body at least in part, the sleeve element, at the distal end thereof, having a contact portion which is in contact with at least a portion of a patient's skin when using the syringe and which defines an opening face, wherein:
      at least a portion of the opening face comprises a segment which forms an angle α together with the axial direction (X), the angle α being in a range between 10° and 80°, the safety device comprising a collar element which is rotatably arranged on the distal end region of the syringe body and locks the safety device on the syringe body along the axial direction (X),
      the collar element comprises at least one guide projection which engages in at least one guide track of the sleeve element, the guide projection being guided in the at least one guide track of the sleeve element substantially in the axial direction (X) when the syringe body moves relative to the sleeve element, movement of the syringe body relative to the sleeve element and the guidance of the guide projection in the guide track causes the collar element to rotate in a circumferential direction (U) of the syringe body,
      the guide track comprises a first and a second track region which are separated from one another by a fictive separating line extending along the axial direction (X) of the syringe body, the guide projection, in a starting position, being arrangeable in the first track region,
   in the starting position, a distal end of the piercing means is arranged inside the sleeve element in the axial direction (X), and the guide projection is able to be moved from the first track region into an end position in the second track region by crossing the separating line when a distal end of the piercing means is arranged in the opening face when the syringe body moves relative to the sleeve element,
   the guide projection is able to be moved, by means of a track of the second track region, from the second track region into an end region, in which movement of the sleeve element relative to the syringe body substantially along the axial direction (X) is at least limited, and a further distal displacement of the sleeve element relative to the syringe body is prevented by an abutment of the guide projection to the end region of the guide track, and
   the guide projection in the end region is substantially at the same height along an axial direction (X) as the guide projection in the starting position.

* * * * *